United States Patent
Nagasaka

(10) Patent No.: US 8,362,768 B2
(45) Date of Patent: Jan. 29, 2013

(54) MAGNETIC SENSOR

(75) Inventor: Kimio Nagasaka, Hokuto (JP)

(73) Assignee: Seiko Epson Corporation, Tokyo (JP)

( * ) Notice: Subject to any disclaimer, the term of this patent is extended or adjusted under 35 U.S.C. 154(b) by 493 days.

(21) Appl. No.: 12/759,967

(22) Filed: Apr. 14, 2010

(65) Prior Publication Data

US 2010/0327865 A1    Dec. 30, 2010

(30) Foreign Application Priority Data

Jun. 26, 2009 (JP) ................................. 2009-152064

(51) Int. Cl.
G01V 3/00 (2006.01)
(52) U.S. Cl. ........................ 324/304; 324/300
(58) Field of Classification Search .......... 324/300–322, 324/69; 600/4, 7, 445; 505/162, 486; 385/142
See application file for complete search history.

(56) References Cited

U.S. PATENT DOCUMENTS

| | | | |
|---|---|---|---|
| 6,414,473 B1 * | 7/2002 | Zhang et al. | 324/96 |
| 6,573,700 B2 * | 6/2003 | Zhang et al. | 324/96 |
| 7,495,435 B2 * | 2/2009 | Appelt et al. | 324/300 |
| 7,656,154 B2 * | 2/2010 | Kawabata et al. | 324/244.1 |
| 7,710,114 B2 * | 5/2010 | Hattori et al. | 324/304 |
| 2010/0327862 A1 * | 12/2010 | Nagasaka | 324/244.1 |
| 2011/0037454 A1 * | 2/2011 | Han et al. | 324/96 |
| 2011/0128002 A1 * | 6/2011 | Fujiwara et al. | 324/318 |

FOREIGN PATENT DOCUMENTS

| | | |
|---|---|---|
| JP | A-2009-162554 | 7/2009 |
| WO | WO 2009/084731 A1 | 7/2009 |

OTHER PUBLICATIONS

Affolderbach, C. et al., "An All-Optical, High-Sensitivity Magnetic Gradiometer," Applied Physics B, 2002, pp. 605-612, vol. 75.
Bison, G. et al., "A Laser-Pumped Magnetometer for the Mapping of Human Cardio-Magnetic Fields," Applied Physics B (Chapter 3), 2003, pp. 43-51, vol. 76.

* cited by examiner

Primary Examiner — Brij Shrivastav
(74) Attorney, Agent, or Firm — Oliff & Berridge, PLC

(57) ABSTRACT

A magnetic sensor for measuring a magnetic field using an optical pumping method includes a first gas in which a valence electron is composed of an odd number of atoms or ions, a probe light incidence device which causes first probe light including straight polarized light to be incident on the first gas, a second gas in which a valence electron arranged on an optical path of second probe light that is the first probe light transmitted through the first gas is composed of an odd number of atoms or ions, a pumping light incidence device which causes first pumping light including first circular polarized light to be incident on the first gas and second pumping light including second circular polarized light to be incident on the second gas, and a detector which detects a rotation angle of a polarization plane of the first probe light and a polarization plane of third probe light that is the second probe light transmitted through the second gas.

6 Claims, 5 Drawing Sheets

MAGNETIC SENSOR

BACKGROUND

1. Technical Field

The present invention relates to a magnetic sensor or the like.

2. Related Art

In the related art, a biomagnetism detecting apparatus has been known that measures a minute magnetic field occurring from a living subject, such as cardiac magnetism (magnetism coming from a heart), cerebral magnetism (magnetism coming from a brain), and the like. As such a biomagnetism detecting apparatus, for example, there is a Superconducting QUantum Interference Device (SQUID). Furthermore, the SQUID is a device (magnetic sensor) that can take variations of a slight magnetic field out as an electric voltage under a low temperature environment, by using, for example, a device (Josephson device) in which a thin portion (Josephson junction) is provided in a part of a superconducting device such as a superconducting ring, or the like.

FIGS. 5A and 5B are schematic diagrams of magnetic flux detecting coils showing an example of the SQUID in the related art. FIG. 5A is a diagram showing a magnetic flux detecting coil (magnetometer), which is wound once. FIG. 5B is a diagram showing a magnetic flux detecting coil that two parallel coils wound in opposite directions to each other are connected in series (first-order gradient type gradiometer).

As shown in FIG. 5A, in a magnetometer 101, a magnetic field 110 coming into the coil is totally detected. Therefore, in order to detect only a magnetic field (for example, cardiac magnetism or cerebral magnetism) generated from near the coil, it is necessary to prepare a separate method of completely eliminating a noise by a magnetic field having the source distant from the coil (for example, external magnetic noise).

As shown in FIG. 5B, in a first-order gradient type gradiometer 102, the magnetic field 110 is detected as a difference of detection signals detected from the two coils wound in the opposite directions to each other. For this reason, the influence of the magnetic field having the source distant from the coils is negated and becomes zero between the two coils, and only the magnetic field generated from near the coils is detected. However, the SQUID costs are high because a superconducting device or a Josephson device is used. In addition, the SQUID needs an effort because it is necessary to frequently supply liquid helium or liquid nitrogen to a cooling system in order to maintain a low temperature environment.

On the other hand, there is an optically-pumped atomic magnetometer as a method of measuring a micro-magnetic field without using the SQUID. The optically-pumped atomic magnetometer is an apparatus that measures a magnetic field by detecting a magnetization state of an atom by causing an atom and a magnetic field to interact with each other using an optical pumping method (a method in which an electron spin of atoms is polarized using polarized light and the polarized atoms are detected with high sensitivity). For example, in Appl. Phys. B75, 605-612 (2002) and Appl. Phys. B76, 325-328 (2003), two laser beams having polarization directions different from each other are incident on a gas cell into which alkali metal atoms such as cesium and the like are injected, the two laser beams transmitted through the gas cell are each received with two photodetectors to detect light intensities. After that, optical signals detected by the two photodetectors are converted into electric signals to calculate a difference in intensity variations of the laser beams, and thereby measuring a micro-magnetic field excluding an influence of an external magnetic field.

However, in the Appl. Phys. B75, 605-612 (2002) and Appl. Phys. B76, 325-328 (2003), there is a case where a noise occurs when optical signals detected by the two photodetectors are converted into electric signals, and thereby causing difficulties to measure a micro-magnetic field with high accuracy. In addition, since two photodetectors are used as detectors, the structure of a magnetic sensor is complicated and the calculation also becomes complicated.

SUMMARY

An advantage of some aspects of the invention is to provide a magnetic sensor that enables the measurement of a micro-magnetic field with high accuracy and achieves a simplified structure.

According to an aspect of the invention, there is provided a magnetic sensor for measuring a magnetic field using an optical pumping method including a first gas in which a valence electron is composed of an odd number of atoms or ions, a probe light incidence device which causes first probe light including straight polarized light to be incident on the first gas, a second gas in which a valence electron arranged on an optical path of second probe light that is the first probe light transmitted through the first gas is composed of an odd number of atoms or ions, a pumping light incidence device which causes first pumping light including first circular polarized light to be incident on the first gas and second pumping light including second circular polarized light to be incident on the second gas, and a detector which detects a rotation angle of a polarization plane of the first probe light and a polarization plane of third probe light that is the second probe light transmitted through the second gas.

With the configuration, since first pumping light is incident on the first gas and second pumping light is incident on the second gas, the spin polarization is generated in the first gas and the second gas so that the magnetization applied to the first gas and the magnetization applied to the second gas have different orientations from each other. In addition, the rotation angle (Faraday rotation angle) of the polarization plane of the probe light before/after the light is transmitted through the first gas and the second gas is detected. Accordingly, a difference in the magnitude of the spin polarization in the first gas and the magnitude of the spin polarization in the second gas can be obtained. As a result, the influence of an external magnetic field in the first gas and the influence of an external magnetic field in the second gas offset each other, and thereby only a measuring target magnetic field applied to the first gas is measured. In other words, the calculation of a difference in optical signals is performed without converting the optical signals into electric signals as in Appl. Phys. B75, 605-612 (2002) and Appl. Phys. B76, 325-328 (2003). In addition, since two photodetectors are not used as detectors, the structure of the magnetic sensor is simple and the calculation becomes smooth. Therefore, it is possible to provide the magnetic sensor that enables the measurement of a micro-magnetic field with high accuracy and achieves a simplified structure.

Furthermore, according to the above aspect of the invention, there is provided the magnetic sensor in which it is preferable that the pumping light incidence device causes spin polarization to be generated in the first gas and the second gas so that the magnetization in a direction parallel to an optical axis of the first probe light in the first gas and the magnetization in a direction parallel to an optical axis of the second probe light in the second gas have opposite orientations to each other.

With the configuration, the spin polarization is generated in the first gas and the second gas so that the magnetization in the direction parallel to the optical axis of the first probe light in the first gas and the magnetization in the direction parallel to the optical axis of the second probe light in the second gas have opposite orientations to each other. As a result, the influence of the external magnetic field in the first gas is assuredly offset by the influence of the external magnetic field in the second gas, and thereby only a measuring target magnetic field applied to the first gas is assuredly measured. Therefore, it is possible to provide the magnetic sensor that enables the assured measurement of a micro-magnetic field with high accuracy and achieves a simplified structure.

Furthermore, according to the above aspect of the invention, there is provided the magnetic sensor in which it is preferable that the pumping light incidence device causes one of σ+ polarized light and σ− polarized light to be incident on the first gas in a direction orthogonal to both of the magnetic field and the optical axis of the first probe light, and the other one of the σ+ polarized light and the σ− polarized light to be incident on the second gas in a direction orthogonal to both of the magnetic field and the optical axis of the second probe light.

With the configuration, it is possible to assuredly and easily control a state of the spin polarization in the first gas and a state of the spin polarization in the second gas.

Furthermore, according to the above aspect of the invention, there is provided the magnetic sensor in which the pumping light incidence device may include a light source which emits light, and a polarized light separation optical system which separates light emitted from the light source into σ+ polarized light and σ− polarized light and causes one of the σ+ polarized light and the σ− polarized light to be incident on the first gas and the other one of the σ+ polarized light and the σ− polarized light to be incident on the second gas.

With the configuration, it is possible to simplify the structure of the device because the light source that causes light to be incident on the first gas and the light source that causes light to be incident on the second gas can be the same one.

Furthermore, according to the above aspect of the invention, there is provided the magnetic sensor in which the polarized light separation optical system may include a polarized light separation film that separates light emitted from the light source into P-polarized light and S-polarized light, a first retardation plate that gives a phase difference of one-quarter wavelength to one of the P-polarized light and the S-polarized light separated by the polarized light separation film, converts the light into one of the σ+ polarized light and the σ− polarized light, and causes the one of the σ+ polarized light and the σ− polarized light to be incident on the first gas, and a second retardation plate that gives a phase difference of one-quarter wavelength to the other one of the P-polarized light and the S-polarized light separated by the polarized light separation film, converts the light into the other one of the σ+ polarized light and the σ− polarized light, and causes the other one of the σ+ polarized light and the σ− polarized light to be incident on the second gas.

With the configuration, it is possible to provide the polarized light separation optical system at a low cost by using a polarizing beam splitter on the market or a one-quarter wavelength plate.

Furthermore, according to the above aspect of the invention, there is provided the magnetic sensor in which the first gas and the second gas may be injected into the same cell.

With the configuration, since the first gas and the second gas are injected into the same cell, the structure of the device is simpler than a case where the first gas and the second gas are injected into difference cells. In addition, when the first gas and the second gas are injected into difference cells, the alignments of the optical axis of the probe light and each cell have to be performed separately from each other, but when the first gas and the second gas are injected into the same cell, such alignment is completed for one time, and therefore, the setting becomes easy.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
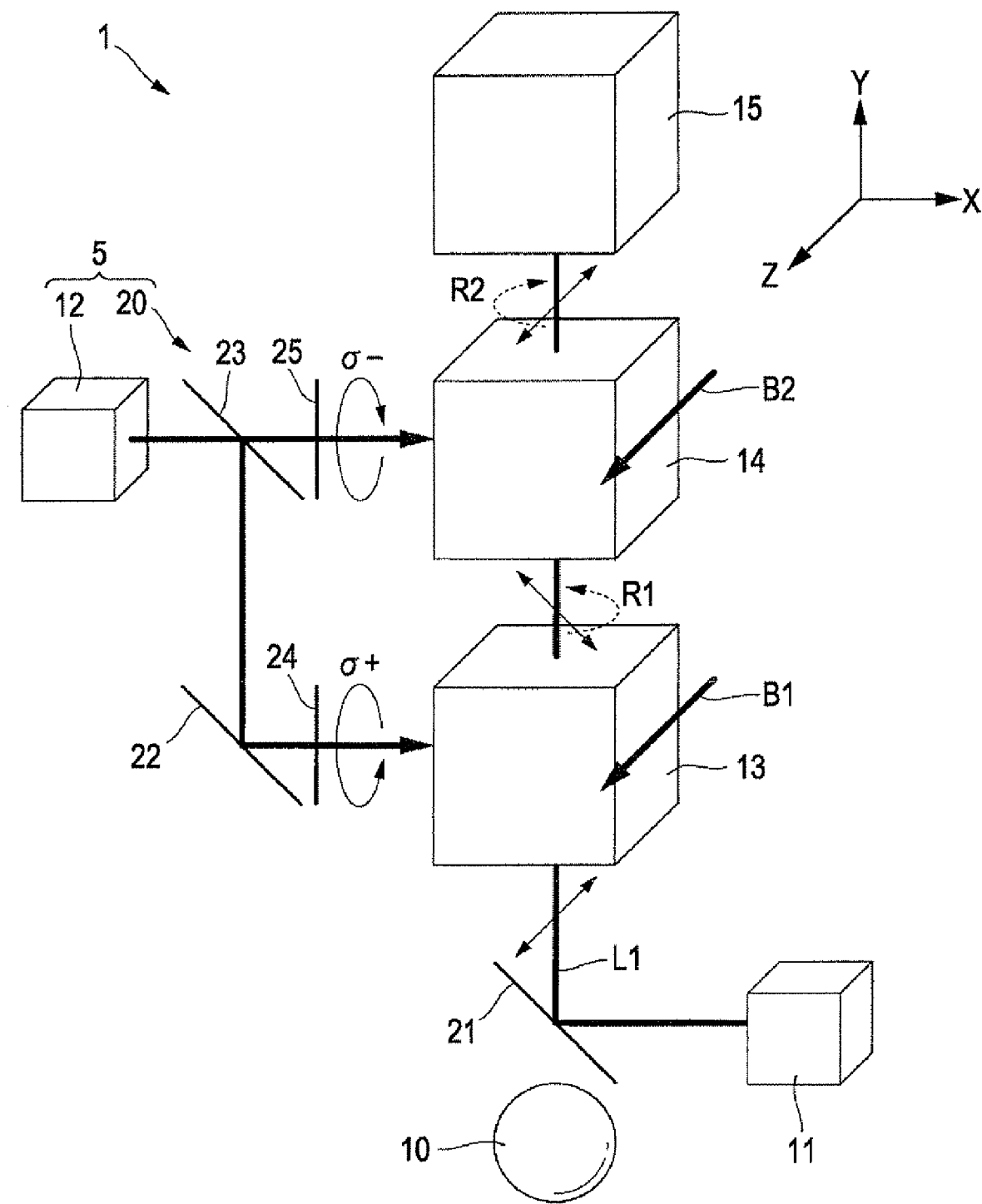
FIG. 1 is a schematic diagram showing a magnetic sensor according to an embodiment of the invention.

Hereinafter, an embodiment of the invention will be described with reference to accompanying drawings. The embodiment is to show an aspect of the invention, and the invention is not limited thereto. The invention can be arbitrarily modified within the scope of the gist of the invention. In addition, in the drawings below, the scales, the numbers, and the like of the structure are difference from those of the actual structure of the invention in order to provide easy understanding about the structure.

FIG. 1 is a schematic diagram showing the outline of the structure of a magnetic sensor 1 according to an embodiment of the invention. As shown in FIG. 1, the magnetic sensor 1 is an apparatus for measuring a measuring target magnetic field (a micro-magnetic field occurring from a magnetic field source 10, for example, cardiac magnetism or cerebral magnetism) using the optical pumping method (a method in which an electron spin of atoms is polarized using polarized light and the polarized atoms are detected with high sensitivity). In addition, in the description to be provided below, the composition and arrangement of each constituent member will be described using an XYZ orthogonal coordinate system in which the direction of the measuring target magnetic field is a Z-axis, and two directions of a plane orthogonal to the Z-axis are an X-axis and a Y-axis.

The magnetic sensor 1 includes a first cell 13, a second cell 14, a probe light incidence device 11, a pumping light incidence device 5, and a detector 15.

The first cell 13 and the second cell 14 are arranged together in series in the Y-axis direction. The second cell 14 is arranged on an optical path of a probe light L1 that has been transmitted through a first cell 13 (a second probe light). The first cell 13 is arranged in a position relatively close to the magnetic field source 10, and the second cell 14 is arranged in a position relatively far from the magnetic field source 10. The first cell 13 is applied with a magnetic field B1 that is a synthetic magnetic field of an external magnetic field and a measuring target magnetic field in the Z-axis direction. The second cell 14 is applied with a magnetic field B2 that is a synthetic magnetic field of an external magnetic field and a measuring target magnetic field in the Z-axis direction. Here, since the second cell 14 is arranged in a position far from the magnetic field source 10, the measuring target magnetic field applied to the second cell 14 is as small as to be ignored. In other words, it is possible to regard that the second cell 14 is applied only with the external magnetic field in the Z-axis direction.

In the first cell 13 and the second cell 14, a first gas and a second gas each of which a valance electron is composed of an odd number of atoms or ions are injected. In the present embodiment, the first gas and the second gas include alkali metal atoms such as potassium, rubidium, cesium, or the like. In addition, in order to intensify the density of the alkali metal atoms in the first cell 13 and the second cell 14, the first cell 13 and the second cell 14 may be heated depending on the necessity.

Moreover, in the first cell 13 and the second cell 14, at least one gas of a rare gas such as neon, helium, argon, xenon, or the like and a non-magnetic gas such as hydrogen, nitrogen, or the like may be injected. Accordingly, it is alleviated that the alkali metal atoms injected into the first cell 13 and the second cell 14 collide with one another or with an inner wall of the cells.

The probe light incident device 11 is a laser radiating device that emits straight polarized light. The probe light incidence device 11 causes the probe light L1 (first probe light) composed of straight polarized light oscillating in a direction (Z-axis direction) parallel with the magnetic field B1 to be incident on the first cell 13 via a reflective mirror 21 in a direction (Y-axis direction) orthogonal to the magnetic field B1.

The pumping light incidence device 5 has a function of bring about spin polarization to the first gas and the second gas so that magnetization in a direction parallel to the optical axis of the probe light L1 given to the first gas in the first cell 13 (first probe light) and magnetization in a direction parallel to the optical axis of the probe light L1 given to the second gas in the second cell 14 (second probe light) are oriented opposite to each other by causing pumping light composed of circular polarized light to be incident on the first cell 13 and the second cell 14.

The pumping light incidence device 5 has a function of causing one of σ+ polarized light (right circular polarized light which is clockwise circular polarized light with respect to an advancing direction of light along the X-axis) and σ− polarized light (left circular polarized light which is counterclockwise circular polarized light with respect to the advancing direction of light along the X-axis) to be incident on the first cell 13 in a direction (X-axis direction) orthogonal to both of the magnetic fields B1 and B2 and the optical axis of the probe light L1 (first probe light). On the other hand, the pumping light incidence device 5 has a function of causing the other one of σ+ polarized light and σ− polarized light to be incident on the second cell 14 in a direction (X-axis direction) orthogonal to both of the magnetic fields B1 and B2 and the optical axis of the probe light L1 (second probe light). The pumping light incident device 5 of the embodiment causes σ+ polarized light (first pumping light) to be incident on the first cell 13 and σ− polarized light (second pumping light) to be incident on the second cell 14.

The pumping light incidence device 5 is provided with a light source 12 that emits light and a polarized light separation optical system 20 that separates light emitted from the light source 12 into σ+ polarized light and σ− polarized light and causes one of the σ+ polarized light and the σ− polarized light to be incident on the first cell 13 and the other one to be incident on the second cell 14. The polarized light separation optical system 20 of the embodiment causes the σ+ polarized light to be incident on the first cell 13 and the σ− polarized light to be incident on the second cell 14.

The light source 12 is a light source that emits light including P-polarized light and S-polarized light. The polarized light separation optical system 20 is provided with a polarized light separation film 23, a first retardation plate 24, a second retardation plate 25, and a reflective mirror 22. The polarized separation film 23 has a function of separating light emitted from the light source 12 into P-polarized light and S-polarized light. The polarized light separation film 23 is composed of, for example, a polarizing beam splitter (PBS). The first retardation plate 24 has a function of giving a phase difference of a one-quarter wavelength to one of P-polarized light and S-polarized light separated by the polarized light separation film 23, converting the one of the P-polarized light and the S-polarized light into one of σ+ polarized light and σ− polarized light, and then causing the one of the σ+ polarized light and the σ− polarized light to be incident on the first cell 13. The second retardation plate 25 has a function of giving a phase difference of a one-quarter wavelength to the other one of P-polarized light and S-polarized light separated by the polarized light separation film 23, converting the other one of the P-polarized light and the S-polarized light into the other one of σ+ polarized light and σ− polarized light, and then causing the other one of the σ+ polarized light and the σ− polarized light to be incident on the second cell 14.

The first retardation plate 24 of the embodiment gives a phase difference of one-quarter wavelength to the S-polarized light separated by the polarized light separation film 23, converts the S-polarized light into σ+ polarized light, and causes the σ+ polarized light to be incident on the first cell 13. On the other hand, the second retardation plate 25 gives a phase difference of one-quarter wavelength to the P-polarized light separated by the polarized light separation film 23, converts the P-polarized light into σ− polarized light, and causes the σ− polarized light to be incident on the second cell 14.

When light including the P-polarized light and the S-polarized light emitted from the light source 12 in the X-axis direction is incident on the polarized light separation film 23, the S-polarized light which is one of polarized light components is reflected on the polarized light separation film 23 and the P-polarized light which is the other one of polarized light components is transmitted through the polarized light separation film 23. The S-polarized light reflected on the polarized light separation film 23 is incident on the first retardation plate 24 via the reflective mirror 22, given with a phase difference of one-quarter of wavelength, and converted into the σ+ polarized light. In addition, the σ+ polarized light is incident on the first cell 13 in parallel to the X-axis direction. On the other hand, the P-polarized light transmitted through the polarized light separation film 23 is incident on the second retardation plate 25, given with a phase difference of one-quarter of wavelength, and converted into the σ− polarized light. In addition, the σ− polarized light is incident on the second cell 14 in parallel to the X-axis direction. In the embodiment, the σ+ polarized light and the σ− polarized light are supposed to be incident on the first cell 13 into which the first gas is injected and on the second cell 14 into which the second gas is injected respectively, but it does not matter that the σ+ polarized light and the σ– polarized light are to be incident on the second cell 14 into which the second gas is injected and on the first cell 13 into which the first gas is injected.

The magnetic sensor 1 of the embodiment adopts a transverse optical pumping with which the incidence direction of the σ+ polarized light and the σ– polarized light each of which is incident on the first cell 13 and the second cell 14 (X-axis direction) is orthogonal to the direction in which the magnetic fields B1 and B2 are applied (Z-axis direction).

The detector 15 has a function of detecting a rotation angle between a polarization plane of the first probe light and a polarization plane of the third probe light which is the second probe light transmitted through the second cell 14 (a rotation angle of a polarization plane of the probe light L1 before/after the light is transmitted through the first cell 13 and the second cell 14) (Faraday rotation angle). The detector 15 is provided with a PBS (polarizing beam splitter), and a photodetector. In addition, a Wollaston prism can be used instead of the PBS. Moreover, it is possible to measure only a micro-magnetic field occurring from the magnetic field source 10 by separating the polarized light components of the probe light L1 composed of straight polarized light with the PBS and electrically calculating a difference of light amounts with the photodetector. In the embodiment, two photodetectors are not used as detectors different from Appl. Phys. B75, 605-612 (2002) and Appl. Phys. B76, 325-328 (2003).

Figure 2A:
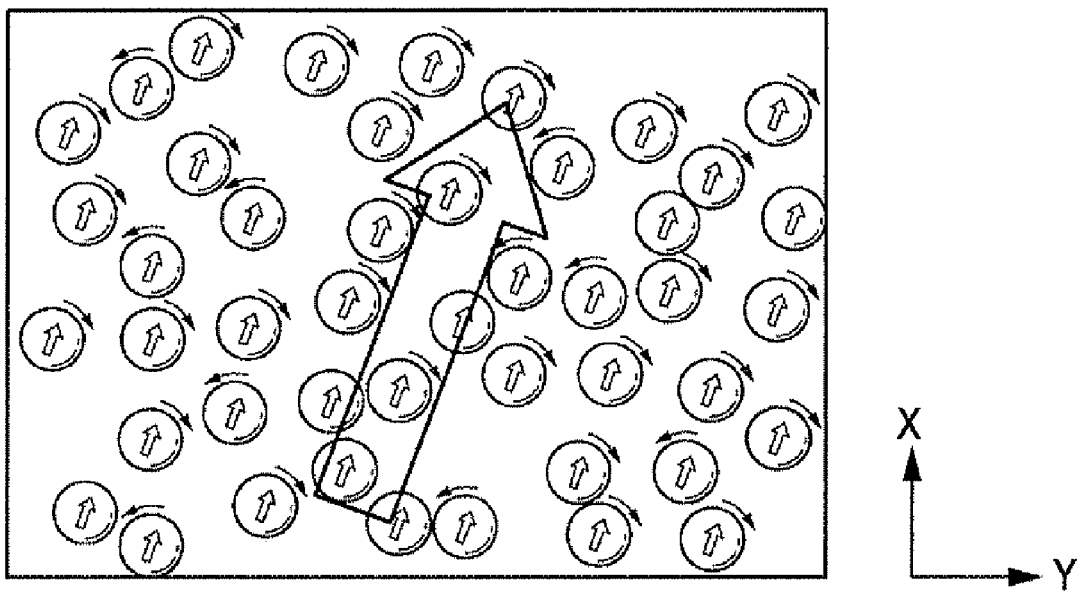
FIGS. 2A and 2B are diagrams showing variations of a magnetization vector of atoms in a first cell.
Figure 2B:
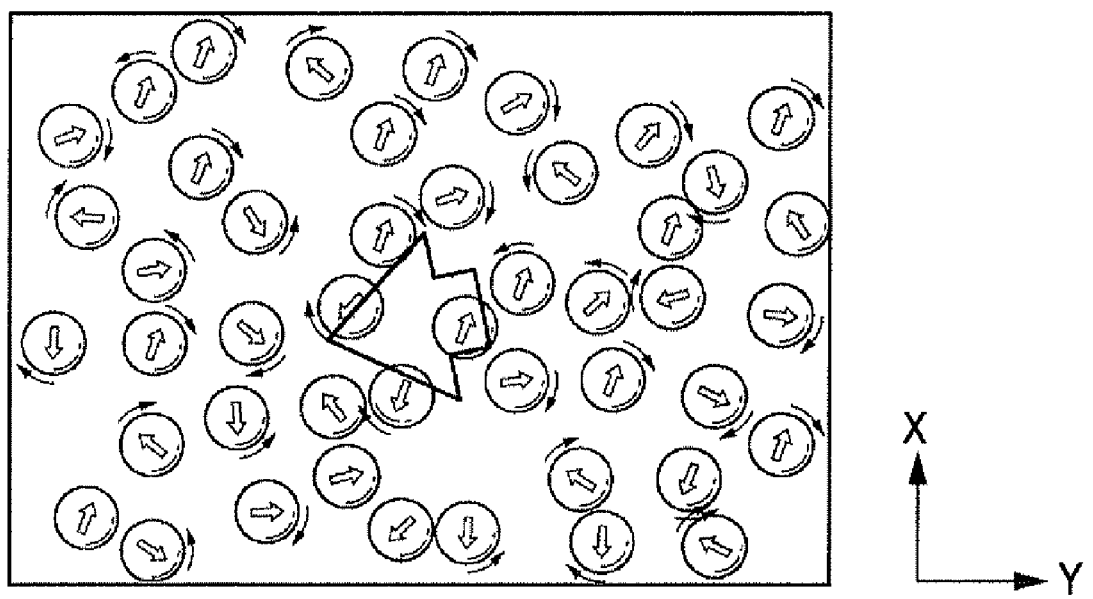

FIGS. 2A and 2B are diagrams showing variations of a magnetization vector of the alkali metal atoms in the first cell 13 after the σ+ polarized light emitted from the pumping light incidence device 5 in the X-axis direction is incident on the first cell 13. FIG. 2A is a diagram showing the magnetization vector of the alkali metal atoms right after the σ+ polarized light is incident on the first cell 13. FIG. 2B is a diagram showing the magnetization vector of the alkali metal atoms when time passes a little while after the σ+ polarized light is incident on the first cell 13.

As shown in FIG. 2A, when the σ+ polarized light is incident on the first cell 13 in the X-axis direction, outermost electrons of the alkali metal atoms are spin-polarized. Specifically, since the σ+ polarized light in the X-axis direction has angular momentum of $+h/2\pi$ (wherein, h is a Planck's constant), the alkali metal atoms that have absorbed the σ+ polarized light temporarily maintain the angular momentum of $+h/2\pi$ and the magnetic moment is oriented in the positive direction of the X-axis. Here, the magnetization vector in the first cell 13 is expressed by the sum of the magnetic moments of a number of the alkali metal atoms. Since the direction of the magnetic moment of each alkali metal atom is toward almost the positive direction of the X-axis in the first cell 13, and accordingly, the direction of the magnetization vector is toward the positive direction of the X-axis and strong magnetization is formed in the positive direction of the X-axis.

As shown in FIG. 2B, after the σ+ polarized light is incident on the first cell 13 and time passes a little while, the electron spin of the alkali metal atoms starts Larmor precession and rotates in an X-Y plane resulting from the action of the magnetic field B1 applied to the first cell 13 in the Z-axis direction. Since frequencies of the Larmor precession (Larmor frequencies) in the electron spin of each alkali metal atom are different in the first cell 13, the direction of the magnetic moment of each alkali metal atom varies. If the direction of the magnetic moment of each alkali metal atom is toward a random direction, the magnetization vector becomes small accordingly, and finally the magnetization disappears (transverse relaxation). Furthermore, the rate from the occurrence of the magnetization vector in the X-Y plane to the disappearance is called a transverse relaxation rate.

Figure 3:
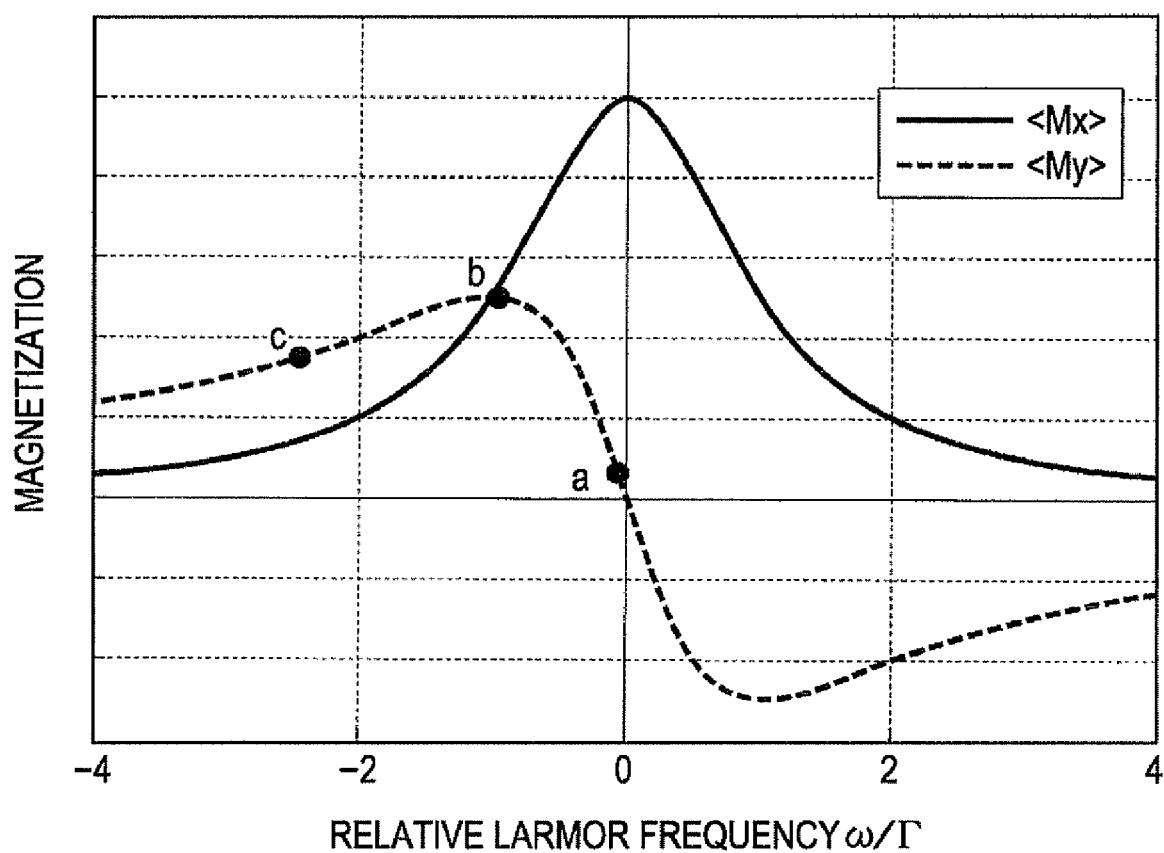
FIG. 3 is a graph showing the relation between relative Larmor frequency and magnetization.

FIG. 3 is a graph showing the relation between the relative Larmor frequency and the magnetization in the transverse optical pumping. In FIG. 3, the horizontal axis represents the relative Larmor frequency and the vertical axis represents the magnetization. Here, the relative Larmor frequency is expressed by W/V on the assumption that a Larmor frequency is indicated by W and a transverse relaxation rate is indicated by V. The solid line Mx in FIG. 3 represents an X-axis direction component of the magnetization vector and the broken line My represents a Y-axis direction component of the magnetization vector.

As shown in FIG. 3, the X-axis direction component Mx of the magnetization vector forms a mountain-shaped curve and becomes at the maximum when the relative Larmor frequency is 0. On the other hand, the Y-axis direction component My of the magnetization vector becomes at the maximum when the relative Larmor frequency is –1, and becomes at the minimum when the relative Larmor frequency is 1. The point a on the broken line My in FIG. 3 represents magnetization when the Larmor frequency W is relatively small than the transverse relaxation rate V (W<<V). In addition, the point b represents magnetization (maximum value) when the Larmor frequency W is almost equal to the transverse relaxation rate V (W≈V). Furthermore, the point c represents magnetization when the Larmor frequency W is greater than the transverse relaxation rate V (W>V).

Figure 4A:
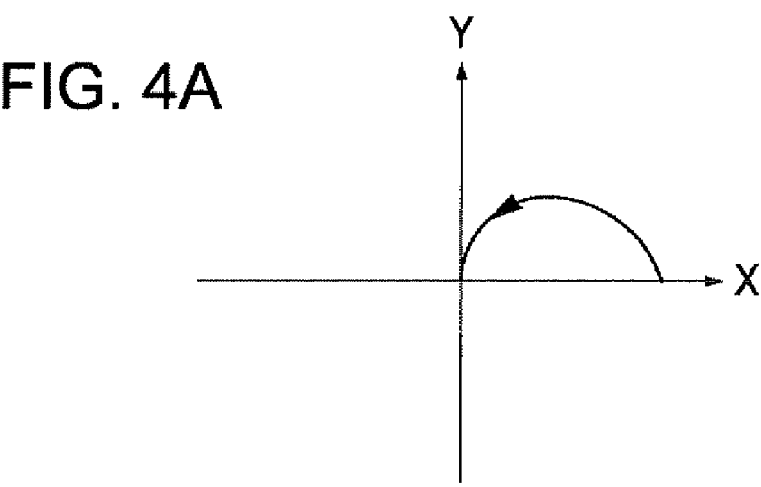
FIGS. 4A to 4C are diagrams showing trajectories of magnetization vectors after optical pumping.
Figure 4B:
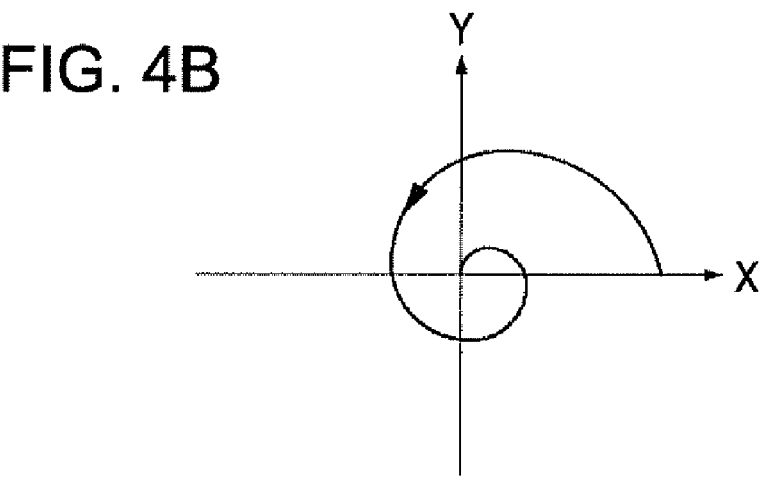
Figure 4C:
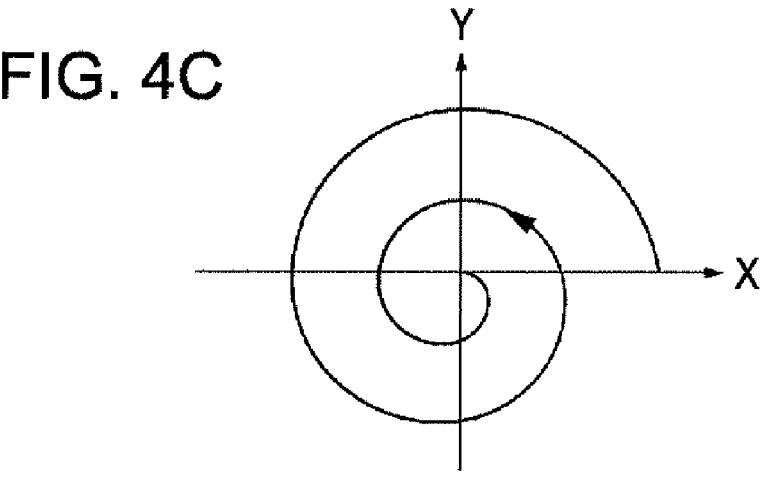
Figure 5A:
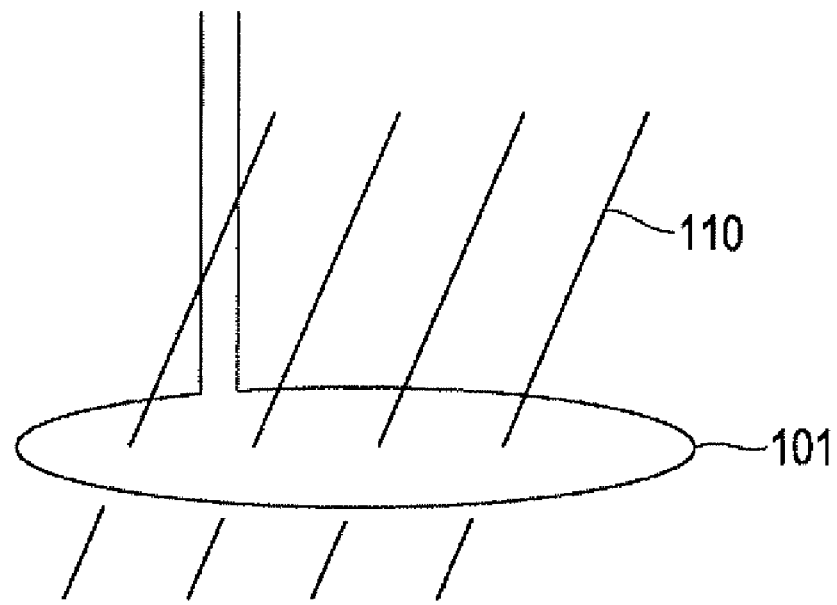
FIGS. 5A and 5B are schematic diagrams of magnetic flux detecting coils showing an example of SQUID in the related art.
Figure 5B:
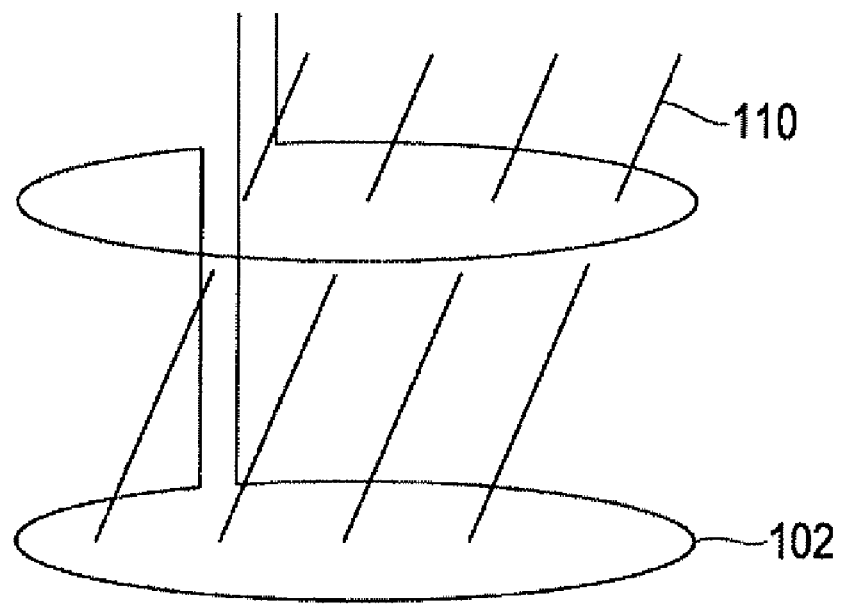

FIGS. 4A to 4C are diagrams shown trajectories of the magnetization vector in the X-Y plane after the optical pumping. FIG. 4A is a diagram showing a trajectory of the magnetization vector on the point a (W<<V) on the broken line My in FIG. 3. FIG. 4B is a diagram showing a trajectory of the magnetization vector on the point b (W≈N) on the broken line My in FIG. 3. FIG. 4C is a diagram showing a trajectory of the magnetization vector on the point c (W>V) on the broken line My in FIG. 3. In addition, the origins in FIGS. 4A to 4C represent a case where magnetization does not have a magnetization vector component, that is, a case where an external magnetic field is not applied (the magnetization is zero).

As shown in FIG. 4A, the trajectory of the magnetization vector on the point a (W<<V) forms a semicircle and is toward the origin from a certain point on the X-axis. In addition, the direction of the arrow shows the direction of the Larmor precession of the electron spin of the alkali metal atoms. In other words, a trajectory of a magnetization vector shows a trajectory connecting tips of magnetization vectors (a variance of magnetization vectors).

As shown in FIG. 4B, the trajectory of the magnetization vector on the point b (W≈V) forms a spiral shape, and is toward the origin from a certain point on the X-axis. In addition, as shown in FIG. 4C, the trajectory of the magnetization vector on the point c (W>V) forms a bigger spiral shape than that in FIG. 4B, and is toward the origin from a certain point on the X-axis.

Here, when the magnetic field B1 applied to the first cell 13 is a weak magnetic field B1 (around the point a in FIG. 3), the Y-axis direction component My of the magnetization vector in proportion to the intensity of the magnetic field B1 is generated. At that time, the Y-axis direction component My of the magnetization vector has a negative value. When the trajectory of the magnetization vector in the point a (W<<V) in FIG. 4A is checked, it is confirmed that the direction of the arrow is oriented to the negative direction of the Y-axis around the origin, and the Y-axis direction component My of the magnetization vector has a negative value.

On the other hand, not shown in the drawing, if the σ− polarized light is incident on the second cell 14 in the X-axis direction, since the σ− polarized light in the X-axis direction has angular momentum of −h/2π (wherein, h is a Planck's constant), the alkali metal atoms that have absorbed the σ− polarized light temporarily maintain the angular momentum of −h/2π and the magnetic moment is oriented in the negative direction of the X-axis. Here, the magnetization vector in the second cell 14 is expressed by the sum of the magnetic moments of a number of the alkali metal atoms. Since the direction of the magnetic moment of each alkali metal atom is toward almost the negative direction of the X-axis in the second cell 14, and accordingly, the direction of the magnetization vector is toward the negative direction of the X-axis and strong magnetization is formed in the negative direction of the X-axis.

In this case, the rotation direction of the Larmor precession of the electron spin of the alkali metal atoms in the second cell 14 is the same rotation direction as that in the first cell 13 described above. Therefore, the Y-axis direction component My of the magnetization vector in the second cell 14 has the opposite direction to the direction of the magnetization vector in the first cell 13 described above, and thereby having a positive value. In other words, the Y-axis direction components My of the magnetization vector in the first cell 13 and the magnetization vector in the second cell 14 have opposite orientations (different in the positive and negative directions).

As shown in FIG. 1, after the straight polarized light oscillating in the Z-axis direction around the Y-axis as a central axis emitted from the probe light incidence device 11 is transmitted through the first cell 13, the polarization plane of the straight polarized light rotates in an X-Z plane (Faraday rotation) by the action of the magnetization vector in the first cell 13. Specifically, after the straight polarized light is transmitted through the first cell 13, the polarization plane of the straight polarized light rotates in an R1 direction (clockwise) around the Y-axis in the X-Z plane because the Y-axis direction component My of the magnetization vector in the first cell 13 has a negative value. Furthermore, the rotation angle (Faraday rotation angle) in the X-Z plane of the polarization plane of the straight polarized light has a proportional relation with the Y-axis direction component My of the magnetization vector.

Furthermore, after the straight polarized light is transmitted through the second cell 14, the polarization plane of the straight polarized light rotates the opposite direction to the rotation direction after the straight polarized light is transmitted through the first cell 13 described above in the X-Z plane, by the action of the magnetization vector in the second cell 14. Specifically, after the straight polarized light is transmitted through the second cell 14, the polarization plane of the straight polarized light rotates in an R2 direction (counterclockwise) around the Y-axis in the X-Z plane because the Y-axis direction component My of the magnetization vector in the second cell 14 has a positive value.

As described above, since the Y-axis direction components My of the magnetization vector in the first cell 13 and the magnetization vector in the second cell 14 have opposite orientations, the Faraday rotation angle after the straight polarized light is transmitted through the first cell 13 and the Faraday rotation angle after the straight polarized light is transmitted through the second cell 14 have opposite rotation directions.

In addition, the Faraday rotation angle is in proportion to the intensity of the magnetic field. Specifically, the Faraday rotation angle after the straight polarized light is transmitted through the first cell 13 is in proportion to the intensity of the magnetic field B1 applied to the first cell 13. Furthermore, the Faraday rotation angle after the straight polarized light is further transmitted through the second cell 14 is in proportion to the intensity of the magnetic field B2 applied to the second cell 14. For that reason, by detecting the Faraday rotation angle after the straight polarized light is transmitted through the second cell 14 with the detector 15, it is possible to obtain a difference between the magnetic field B1 applied to the first cell 13 and the magnetic field B2 applied to the second cell 14 (B1-B2). In the embodiment, the calculation of a difference in optical signals is performed without converting the optical signals into electric signals as shown in Appl. Phys. B75, 605-612 (2002) and Appl. Phys. B76, 325-328 (2003). Therefore, the external magnetic field applied to the first cell 13 is offset by the external magnetic field applied to the second cell 14, and as a result, a measuring target magnetic field applied to the first cell 13 can be obtained.

According to the magnetic sensor 1 of the embodiment, spin polarization occurs in the first gas and the second gas so that the magnetization in the direction parallel to the optical axis of the first probe light in the first cell 13 and the magnetization in the direction parallel to the optical axis of the second probe light in the second cell 14 have opposite orientations to each other. In addition, the rotation angle (Faraday rotation angle) of the polarization plane of the probe light L1 before/after the light is transmitted through the first gas and the second gas is detected. Accordingly, a difference between the magnetic field B1 applied to the first cell 13 and the magnetic field B2 applied to the second cell 14 (B1-B2) is obtained. As a result, the external magnetic field applied to the first cell 13 is offset by the external magnetic field applied to the second cell 14, and the measuring target magnetic field applied to the first cell 13 is measured. In other words, the calculation of a difference in optical signals is performed without converting the optical signals into electric signals as shown in Appl. Phys. B75, 605-612 (2002) and Appl. Phys. B76, 325-328 (2003). In addition, since two photodetectors are not used as detectors, the structure of the magnetic sensor is simplified and the calculation is smooth. Therefore, it is possible to provide the magnetic sensor 1 that enables the measurement of a micro-magnetic field with high accuracy and achieves a simplified structure.

Furthermore, the magnetic sensor 1 of the embodiment is composed of two cells one of which is the first cell 13 into which the first gas is injected and the other one of which is the second cell 14 into which the second gas is injected, but is not limited thereto. For example, the first gas and the second gas may be injected into the same cell.

According to the configuration, since the first gas and the second gas are injected into the same cell, it is possible to provide the magnetic sensor 1 that enables the measurement of a micro-magnetic field with high accuracy and achieves a remarkably simplified structure.

In addition, in the magnetic sensor 1 of the embodiment, the pumping light incidence device 5 causes the σ+ polarized light to be incident on the first cell 13 in the X-axis direction and the σ− polarized light to be incident on the second cell 14 in the X-axis direction, but is not limited thereto. For example, the pumping light incidence device 5 may cause the σ− polarized light to be incident on the first cell 13 in the X-axis direction and the σ+ polarized light to be incident on the second cell 14 in the X-axis direction. In other words, the pumping light incidence device 5 may cause spin polarization to be generated in the first gas and the second gas by causing pumping light composed of circular polarized light to be incident on the first cell 13 and the second cell 14 so that the magnetization in a direction parallel to the optical axis of the probe light L1 given to the first gas in the first cell 13 and the magnetization in a direction parallel to the optical axis of the probe light L1 given to the second gas in the second cell 14 have opposite orientations to each other.

Furthermore, in the magnetic sensor 1 of the embodiment, the pumping light incidence device 5 causes the σ+ polarized light to be incident on the first cell 13 in the positive direction of the X-axis and the σ− polarized light to be incident on the second cell 14 in the positive direction of the X-axis, but is not limited thereto. For example, the pumping light incidence device 5 may be configured to cause the σ+ polarized light to be incident on the first cell 13 in the positive direction of the X-axis and the σ+ polarized light to be incident on the second cell 14 in the negative direction of the X-axis. In other words, the pumping light incidence device may cause circular polarized light including the same polarized component on the first cell 13 and the second cell 14 in opposite directions to each other along the X-axis.

Furthermore, in the magnetic sensor 1 of the embodiment, the pumping light incidence device 5 causes the spin polarization to be generated in the first gas and the second gas so that the magnetization in a direction parallel to the optical axis of the first probe light in the first cell 13 and the magnetization in a direction parallel to the optical axis of the second probe light in the second cell 14 have opposite orientations to each other, but is not limited thereto. For example, the pumping light incidence device 5 may cause the spin polarization to be generated in the first gas and the second gas so that the magnetization applied to the first cell 13 and the magnetization applied to the second cell 14 have different orientations from each other. With such a configuration, it is possible to provide a magnetic sensor that enables the measurement of a micro-magnetic field with high accuracy and achieves a simplified structure.

What is claimed is:

1. A magnetic sensor for measuring a magnetic field using an optical pumping method, comprising:
    a first gas in which a valence electron is composed of an odd number of atoms or ions;
    a probe light incidence device which causes first probe light including straight polarized light to be incident on the first gas;
    a second gas in which a valence electron arranged on an optical path of second probe light that is the first probe light transmitted through the first gas is composed of an odd number of atoms or ions;
    a pumping light incidence device which causes first pumping light including first circular polarized light to be incident on the first gas and second pumping light including second circular polarized light to be incident on the second gas; and
    a detector which detects a rotation angle of a polarization plane of the first probe light and a polarization plane of third probe light that is the second probe light transmitted through the second gas.

2. The magnetic sensor according to claim 1, wherein the pumping light incidence device causes spin polarization to be generated in the first gas and the second gas so that the magnetization in a direction parallel to an optical axis of the first probe light in the first gas and the magnetization in a direction parallel to an optical axis of the second probe light in the second gas have opposite orientations to each other.

3. The magnetic sensor according to claim 1, wherein the pumping light incidence device causes one of σ+ polarized light and σ− polarized light to be incident on the first gas in a direction orthogonal to both of the magnetic field and the optical axis of the first probe light, and the other one of the σ+ polarized light and the σ− polarized light to be incident on the second gas in a direction orthogonal to both of the magnetic field and the optical axis of the second probe light.

4. The magnetic sensor according to claim 1, wherein the pumping light incidence device includes a light source which emits light, and a polarized light separation optical system which separates light emitted from the light source into σ+ polarized light and σ− polarized light and causes one of the σ+ polarized light and the σ− polarized light to be incident on the first gas and the other one of the σ+ polarized light and the σ− polarized light to be incident on the second gas.

5. The magnetic sensor according to claim 4, wherein the polarized light separation optical system includes a polarized light separation film that separates light emitted from the light source into P-polarized light and S-polarized light, a first retardation plate that gives a phase difference of one-quarter wavelength to one of the P-polarized light and the S-polarized light separated by the polarized light separation film, converts the light into one of the σ+ polarized light and the σ− polarized light, and causes the one of the σ+ polarized light and the σ− polarized light to be incident on the first gas, and a second retardation plate that gives a phase difference of one-quarter wavelength to the other one of the P-polarized light and the S-polarized light separated by the polarized light separation film, converts the light into the other one of the σ+ polarized light and the σ− polarized light, and causes the other one of the σ+ polarized light and the σ− polarized light to be incident on the second gas.

6. The magnetic sensor according to claim 1, wherein the first gas and the second gas are injected in the same cell.

* * * * *